United States Patent [19]

Dysarz et al.

[11] Patent Number: 4,978,343
[45] Date of Patent: Dec. 18, 1990

[54] TRAP IN BARREL ONE HANDED RETRACTABLE SAFETY SYRINGE

[76] Inventors: Edward D. Dysarz, 11423 Triola La., Houston, Tex. 77072; Derek R. Van Gilder, 7906 Quail Meadow Dr., Houston, Tex. 77071

[21] Appl. No.: 488,613

[22] Filed: Mar. 6, 1990

Related U.S. Application Data

[63] Continuation-in-part of Ser. No. 466,722, Jan. 16, 1990.

[51] Int. Cl.5 ............................................. A61M 5/32
[52] U.S. Cl. ................................... 604/195; 604/198; 604/110
[58] Field of Search ............... 604/195, 198, 110, 187, 604/263, 218

[56] References Cited

U.S. PATENT DOCUMENTS

| | | | |
|---|---|---|---|
| 4,747,831 | 5/1988 | Kulli | 604/198 X |
| 4,838,863 | 6/1989 | Allard et al. | 604/195 X |
| 4,850,977 | 7/1989 | Bayless | 604/198 |
| 4,874,382 | 10/1989 | Lindemann et al. | 604/195 |

*Primary Examiner*—John D. Yasko

[57] ABSTRACT

A disposable hypodermic syringe having a needle cannula fixed to a piston assembly. The piston assembly is held within the elongated hollow barrel of said hypodermic syringe by a compressed spring and a trigger. When said trigger is disengaged with said piston assembly said spring pushes said piston assembly and said needle cannula into said barrel of said hypodermic syringe and holds said needle cannula fixed to said piston assembly within said barrel and is further prevented from being pushed out of said elongated hollow barrel by a rim in said elongated hollow barrel thus preventing any accidental injection of bacteria, virus or other undesirable material into others. The disengagement of said trigger with said piston assembly is accomplished with only one and the same hand that is used to inject the needle cannula and medicament into a body.

6 Claims, 2 Drawing Sheets

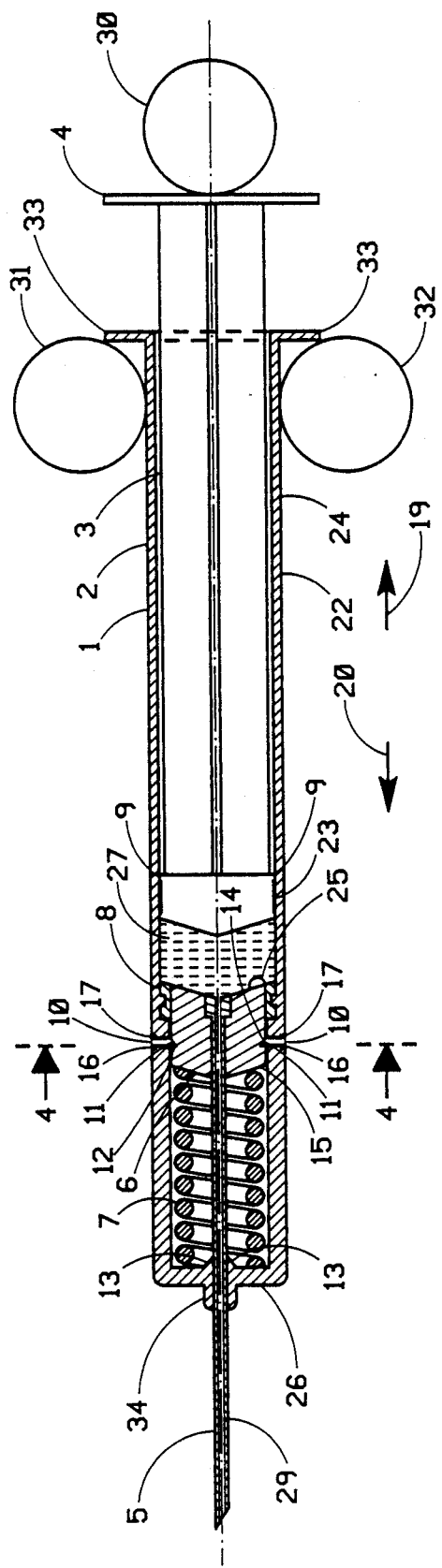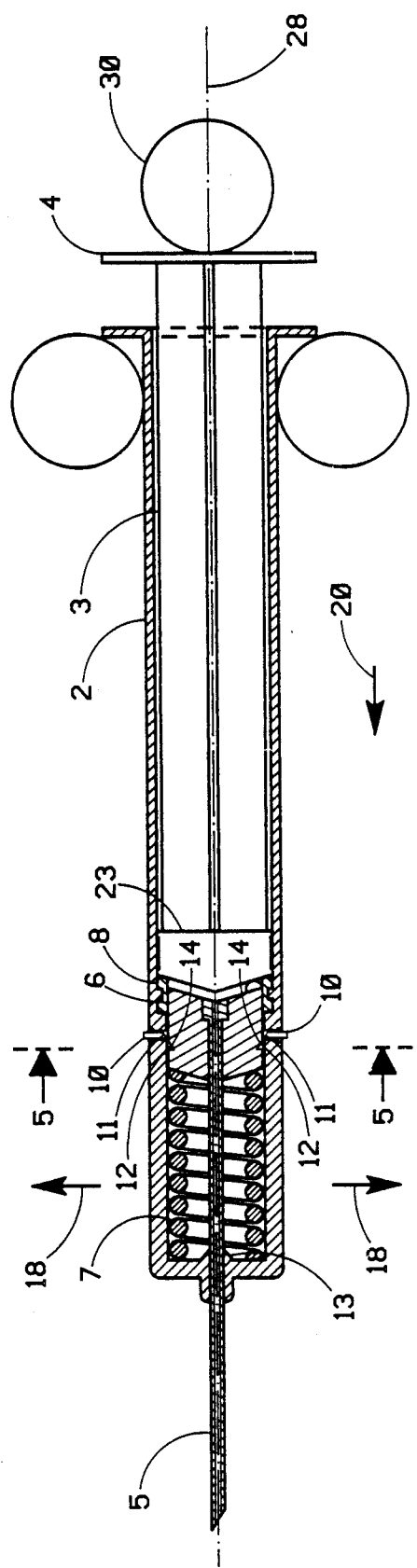

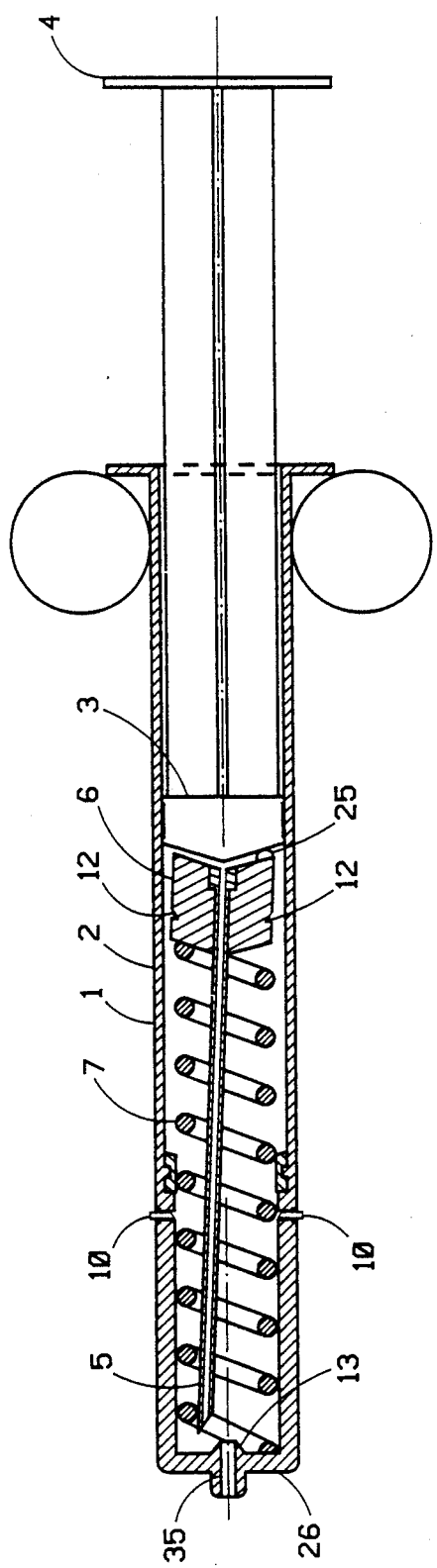
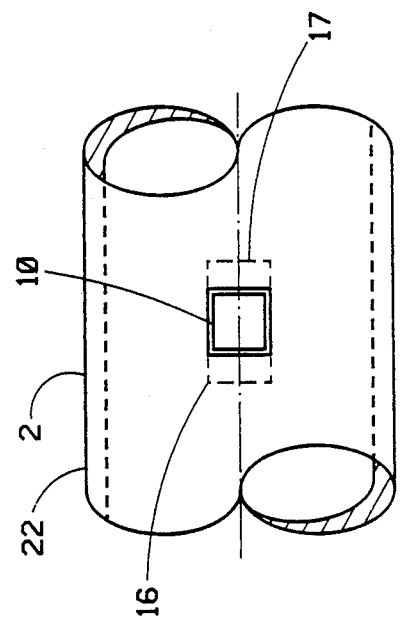
FIGURE 6
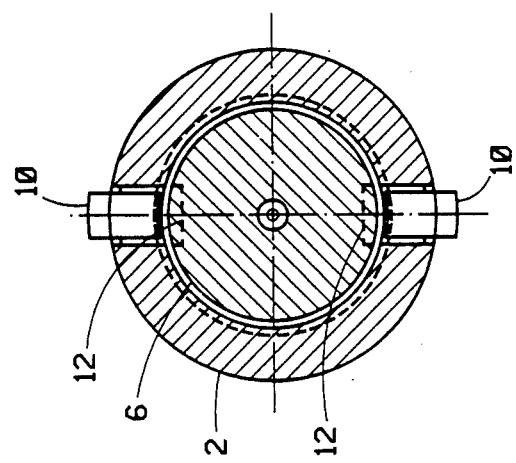
FIGURE 5
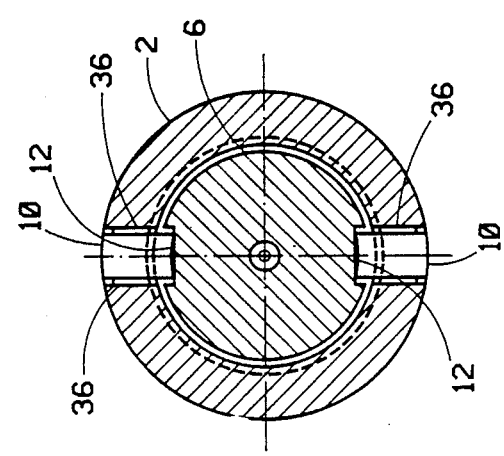
FIGURE 4

TRAP IN BARREL ONE HANDED RETRACTABLE SAFETY SYRINGE

CROSS REFERENCE TO RELATED APPLICATIONS

Continuation in part of U.S. patent application Ser. No. 07/466,722 filed Jan. 16, 1990, of Edward D. Dysarz.

BACKGROUND OF THE INVENTION

There are many safety syringe designs available today. Some of these designs have a sleeve or a sheath that will cover the needle after it has been used. Some typical designs with sleeves or sheaths are Z. M. ROEHR et al U.S. Pat. No. 3,008,570, Z. M. ROEHR U.S. Pat. No. 3,107,785, BARTNER, et al U.S. Pat. No. 3,895,633, G. K. BURKE U.S. Pat. No. 3,306,291, GYURE et al U.S. Pat. No. 4,300,678, WINSTEAD HALL U.S. Pat. No. 4,356,822, SAMPSON U.S. Pat. No. 4,425,120, LARSON U.S. Pat. No. 4,639,249, HARBAUGH U.S. Pat. No. 4,655,751, STRAUSS U.S. Pat. No. 4,664,654, BRAGINETZ U.S. Pat. No. 466,435, SPENCER U.S. Pat. No. 4,702,738, MILORAD U.S. Pat. No. 4,702,739, SPENCER U.S. Pat. No. 4,801,295, PONCY U.S. Pat. No. 4,816,022, and HUGHES U.S. Pat. No. 4,840,619.

Other designs have a retractable needle such as WELTMAN U.S. Pat. No. 3,306,290, and DENT U.S. Pat. No. 4,392,859. These designs do not have a means whereby the needle is extended from the syringe and held in place in a positive and rigid position in order to first inject the needle prior to injecting the medication. Still other designs have methods of bending the needle to render it harmless after the medication has been injected. Most of these designs have one major purpose and that is to prevent the spread of infectious diseases such as aids, hepatitis or other diseases from an accidental injection with a contaminated needle into others after the needle of the syringe was inserted into a patient with the above mentioned disease. These various designs all work well up to a degree, but they all fall short of their intended purpose during the act of covering the needle, or removing the needle, which requires two hands.

All of these designs require at least two hands to operate. The use of two hands to cover the contaminated needle is most unsatisfactory in that during the act of placing a second hand on the syringe the person holding the syringe in one hand may be bumped and accidentally inject the needle into their other hand before it can grasp the syringe. Other accidental jabbing or injections can happen in an ambulance where just as a person tries to grasp the contaminated syringe, the ambulance can hit a bump in the road causing the person holding the syringe to accidentally stick another person or themselves with the contaminated needle. The need has developed for a syringe that will cover the contaminated needle with the use of only one hand.

SUMMARY

It is the object of this invention to provide a syringe wherein the needle of the syringe is retracted into the barrel of the syringe and protects others from an accidental pricking after it has been used; the needle can be retracted into the barrel with the use of only one hand and that one hand being the hand that was used to inject the needle into a patient.

Another object of the present invention is to render the syringe useless after the needle is retracted into the barrel of the syringe and to prevent the accidental reuse of the contaminated syringe or to further prevent the reuse and abuse by users of illicit drugs.

It is still another object of the present invention to further prevent the accidental release of the needle cannula after the needle cannula is in the barrel of the syringe.

The foregoing and other objects and advantages are attained by a hypodermic syringe, syringe barrel, needle, spring, piston assembly, plunger assembly and barrel flange in combination with a trigger means wherein when said syringe is used to inject a drug or other means wherein when said syringe is used to inject a drug or other material into a patient, the trigger is released and the spring further pushes the needle fixed to the piston assembly into the barrel of the syringe rendering the contaminated needle of the syringe harmless to prevent the accidental pricking of others and to prevent the contaminated needle from being released from the barrel of the syringe.

The features of the present invention can be best understood together with further objects and advantages by reference to the following descriptions taken in connection with accompanying drawing, wherein like numerals indicate like parts.

BRIEF DESCRIPTION OF THE DRAWINGS

FIG. 1 is a section elevation view of the preferred embodiment of the present invention.

FIG. 2 is a section elevation view of the preferred embodiment showing the plunger assembly pushing the piston assembly and compressing the spring.

FIG. 3 is an enlarged section elevation view of the preferred embodiment showing the piston assembly with the needle pushed into the barrel of the syringe by the spring.

FIG. 4 is an enlarged section elevation as taken through FIG. 1.

FIG. 5 is an enlarged section elevation as taken through FIG. 2.

FIG. 6 is a partial plan view as taken from FIG. 1.

DETAILED DESCRIPTION OF THE PREFERRED EMBODIMENTS

Referring to FIG. 1 there is shown a section elevation view of the syringe 1 of the preferred embodiment.

The syringe 1 is comprised of an elongated hollow barrel 2 which is a round tube like in configuration with a first end and a second end and with an inner surface 21 and an outer surface 22. Inside of the elongated hollow barrel 2 is the slidable plunger assembly 3. The slidable plunger 3 with a first end and a second end has a thumb flat 4 at the second end and a plunger piston 23 at the first end. The thumb flat 4 is fixed to the plunger piston 23 by the plunger rod 24. The plunger piston 23 also has a plunger gasket 9 which forms a liquid tight and gas tight seal between the plunger piston 23 and the inner surface 21 of the elongated hollow barrel 2.

The elongated hollow barrel 2 has a longitudinal axis 28 in the center of the elongated hollow barrel 2. The longitudinal axis 28 has a first end and a second end and runs the entire length of the elongated hollow barrel 2 from the thumb flat 4 to the needle cannula 5.

Also shown inside of the elongated hollow barrel 2 is the slidable piston 6. The slidable piston 6 is fixed to the needle cannula 5. At the second end of the slidable piston 6 is a pimple 25 which forms part of the slidable piston 6. The slidable piston 6 is shown held in place within the elongated hollow barrel 2 by the trigger 10 and the piston gasket 8. The piston gasket 8 is fixed to the elongated hollow barrel 2 but it could also be fixed to the slidable piston by design choice. The slidable piston 6 is further held in place at the first end by a partly compressed spring 7. The partly compressed spring 7 has a first end resting on the barrel flange 26 and a second end integral with the piston flange 15. The partly compressed spring 7 is pushing on the piston flange 15 of the slidable piston 6. The slidable piston 6 is held and fixed in place by the slidable trigger 10 on each side of the elongated hollow barrel 2.

The syringe 1 is shown held between finger 31 and finger 32 and it is further held and restrained from moving between finger 31 and finger 32 by finger stops 33. The slidable plunger assembly 3 is depressed or pushed by pressure from the thumb 30 on the thumb flat 4.

The slidable plunger assembly 3 is shown moving in a needleward direction 20 forcing medicament 27 through the cannula 29 in the slidable piston 6 and further through the needle cannula 5 into a body not shown or part of a body not shown. The needle cannula 5 is shown with a first end and second end, the first end has a point that will enter a body and the second end is shown fixed to the slidable piston 6.

The spring 7 is shown only partly compressed, with the first end of the spring 7 resting on the barrel flange 26 and the second end of the spring 7 pushing on the piston flange 15. The slidable piston 6 and needle cannula 5 are held firmly and rigidly in the elongated hollow barrel 2 by the combination of the inner rim 13 and the outer rim 34 supporting the needle cannula 5 and the piston gasket 8 supporting the slidable piston 6; this prevents movement of the slidable piston 6 and the needle cannula 5 in a direction perpendicular to the longitudinal axis 28 of the elongated hollow barrel 2. The slidable piston 6 and the needle cannula 5 are also held firmly and rigidly within the elongated hollow barrel 2 by the spring 7 that is partly compressed and is thrusting against the barrel flange 26 and the piston flange 15 in combination with the one or two slidable triggers 10 that restrain the spring 7 from thrusting the slidable piston assembly 6 and needle cannula 5 in a thumbward direction 19.

The slidable trigger 10 has a first end and a second end and is held in place at the first end and supported within the elongated hollow barrel 2 by a left guide 16 and right guide 17. The slidable trigger 10 extends from the left guide 16 and the right guide 17 of the elongated hollow barrel 2 into the trigger notch 12 that is cut into the slidable piston flange 15 of the slidable piston 6.

The slidable trigger 10 is further shown with a trigger slope 11 that slopes in an outward direction 18 and a thumb ward direction 9. The trigger notch 12 has a cut that is perpendicular to the longitudinal axis 28 of the elongated hollow barrel 2 and it also has a trigger notch slope 14 that is parallel to the trigger slope 11 on the second end of the slidable trigger 10. The slidable trigger 10 is held in place within the elongated hollow barrel 2 and the trigger notch 12 by friction or other suitable mean.

Referring to FIG. 2 there is shown a section elevation of the preferred embodiment of the present invention.

The medicament has already been discharged and the needle cannula 5 has been withdrawn from the body not shown or part of the body not shown.

The slidable plunger assembly 3 is pushed further in a needle ward direction 20 by pressure from the thumb 30, on the slidable plunger assembly 3 further pushing the slidable piston 6 and needle cannula 5 in a needle ward direction 20, further compressing the spring 7. As the slidable piston 6 is moved in a needle ward direction 20, the trigger notch slips 14 of the trigger notch 12 reacts with the trigger slope 11 of the sliding trigger 10 thus forcing the sliding trigger 10 to move in an outward direction 18, that is a direction perpendicular to the longitudinal axis 28 of the elongated hollow barrel 2. The piston gasket 8 is shown compressed by the plunger piston 23.

As the slidable trigger 10 is moved in an outward direction 18, it will either fall out or be held in place within the elongated hollow barrel by friction, which is a matter of design choice.

Referring to FIG. 3, there is shown a section elevation of the preferred embodiment of the present invention. The slidable trigger 10 has been moved out of the trigger notch 12 and the thumb shown in FIG. 1 is removed from the thumb flat 4 thus allowing the spring 7 to push the slidable piston 6 and the needle cannula 5 into the elongated hollow barrel 2, where the needle cannula 5 will be completely enclosed by the elongated hollow barrel 2 the barrel flange 26 and the inner rim 13. The spring 7 may have sufficient force to push the slidable plunger assembly 3 partly out of the hollow elongated barrel 2 of the syringe assembly 1.

With the spring 7 constantly pushing or thrusting the slidable piston 6 in a thumbward direction inside the hollow elongated barrel 2, the pimple 25 on the slidable piston 6 forces the slidable piston 6 and the needle cannula 5 to slant relative to the longitudinal axis 28 thereby moving the tip of the needle cannula 5 away from inner rim 13 and the needle cannula tunnel 35 whereby the needle cannula 5 cannot fall to a position where the point of the needle cannula 5 cannot be pushed outside of the confines of the hollow elongated barrel 2, the barrel flange 26 and the inner rim 13.

Referring to FIG. 4, there is shown a section elevation view of the preferred embodiment as taken through FIG. 1. The slidable trigger 10 is shown in the trigger notch 12 of the slidable piston 6. The slidable trigger 10 is also shown in the trigger slot 36 of the elongated hollow barrel 2.

Referring to FIG. 5 there is shown a section elevation view of the first preferred embodiment as taken though FIG. 2. The slidable trigger 10 is shown pushed out from the trigger notch 12 of the slidable piston 6. The slidable trigger 10 is also shown projecting out of the elongated hollow barrel 2 of the syringe 1.

Referring to FIG. 6, there is shown a partial elevation of the outer surface 22 of the hollow elongated barrel 2. The slidable trigger 10 is shown as being square however it could also be round or rectangular by design choice. The left guide 16 and the right guide 17 are shown with hidden lines.

Although the system described in detail supra has been found to be most satisfactory and preferred many variations are possible. For example the syringe may have three or four triggers, the syringe could be square in section or the trigger could be placed closer to the needle.

Although the invention has been described with reference to the preferred embodiment, it will be understood by those skilled in the art, that additions, modifications, substitutions, deletions and other changes not specifically described, may be made in the embodiments herein, it should be understood that the details herein are to be interpreted as illustrative and are not in a limiting sense.

What is claimed as invention is:

1. A syringe held by fingers and thumb for injecting medicament or fluid into a body or part of a body comprising:
    an elongated hollow barrel having a first end and a second end, and having an inner surface and an outer surface and further having a longitudinal axis in the center of the said elongated hollow barrel, parallel in most part of the said inner surface and said outer surface of the said elongated hollow barrel further extending from said first end to said second end of said elongated hollow barrel;
    a slidable plunger assembly inside of said elongated hollow barrel, said slidable plunger assembly having a first end and a second end and further having a plunger piston at said first end and a thumb flat at said second end wherein a thumb or finger pushes on said thumb flat in a direction toward said first end;
    a slidable piston inside of said elongated hollow barrel, said slidable piston having a first end and a second end and said first end of said slidable piston is nearer said first end of said elongated hollow barrel;
    a pimple fixed to said second end of said slidable piston;
    a needle cannula having a first end and a second end, said first end of said needle cannula extends past said first end of said elongated hollow barrel and said second end of said needle cannula is fixed to said first end of said slidable piston;
    a spring means having a first end and a second end, said first end of said spring means is integral with said first end of said elongated hollow barrel and said second end of said spring means is integral with said slidable piston, said spring means is further compressed between said first end of said elongated hollow barrel and said slidable piston;
    at least one trigger notch formed into said slidable piston assembly, said trigger notch further having at least, a first side and a second side, said first side is near perpendicular to said longitudinal axis of said elongated hollow barrel and said first side is nearer to said first end of said slidable piston and said second side of said trigger notch is a trigger notch slope wherein said trigger notch slope is near to said first side of said trigger notch and slopes away from said first side in the direction of said second end of said slidable piston;
    a barrel flange fixed to said first end of said elongated hollow barrel;
    an inner rim fixed to said barrel flange;
    a needle cannula tunnel in said barrel flange and said inter rim;
    at least one slidable trigger, having a first end and a second end, said slidable trigger is held in place within said trigger guide wherein said first end of said slidable trigger is located near the outer surface of said elongated hollow barrel and said slidable trigger further extends past said trigger guide and engages said trigger notch formed into said slidable piston, said second end of said slidable trigger having a slope similar to said trigger notch slope and wherein the said thumb flat of the said slidable plunger assembly is pushed by said finger or thumb and further pushes said plunger into the second end of the said slidable piston further pushing said slidable piston, thereby further compressing the said spring means and further causing the said trigger notch slope to further push on the slope of the said slidable trigger, further causing the said slidable trigger to slide in a direction away from the said longitudinal axis of the said elongated hollow barrel and wherein said sliding trigger no longer engages the said trigger notch and wherein said finger or thumb is further removed from the said thumb flat thus allowing the said spring means to push on the slidable piston which will further push on the slidable plunger assembly thus forcing the needle cannula to move into the first end of the said elongated hollow barrel wherein said pimple on said slidable piston will further thrust into said slidable plunger assembly causing said slidable piston and said needle cannula to slope relative to said longitudinal axis further pointing the tip of said needle cannula away from said needle cannula tunnel completely enclosing said needle cannula within said elongated hollow barrel, said barrel flange and said inner rim wherein said needle cannula cannot be accidentally pushed out of said elongated hollow barrel thus preventing the said needle cannula from accidentally pricking or injuring others.

2. The syringe of claim 1 wherein an outer rim 15 fixed to said barrel flange.

3. The syringe of claim 1 including a gasket means fixed to said elongated hollow barrel.

4. The syringe of claim 1 wherein said gasket means can be compressed by said slidable plunger assembly.

5. The syringe of claim 1 wherein said spring means is only partially compressed while said syringe assembly is being used to inject medicament into a body or part of a body.

6. The syringe of claim 1 wherein said syringe assembly may also be used to draw fluid out of a body or part of body.

* * * * *